US00PP26529P3

(12) United States Plant Patent
Jacobs

(10) Patent No.: US PP26,529 P3
(45) Date of Patent: Mar. 22, 2016

(54) ***CHRYSANTHEMUM* PLANT NAMED 'ZANMUCELES'**

(50) Latin Name: ***Chrysanthemum×morifolium* Ramat.**
Varietal Denomination: Zanmuceles

(71) Applicant: Chrysanthemum Breeders Association Research B.V., Valkenburg ZH (NL)

(72) Inventor: Henricus Cornelius Maria Jacobs, Valkenburg (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 192 days.

(21) Appl. No.: 13/998,967

(22) Filed: Dec. 30, 2013

(65) Prior Publication Data

US 2015/0189812 P1 Jul. 2, 2015

(51) Int. Cl.
*A01H 5/00* (2006.01)

(52) U.S. Cl.
USPC ..... Plt./294

(58) Field of Classification Search
USPC ..... Plt./294
See application file for complete search history.

*Primary Examiner* — Keith Robinson
(74) *Attorney, Agent, or Firm* — Steptoe & Johnson LLP

(57) ABSTRACT

A *chrysanthemum* plant named 'Zanmuceles' characterized by its medium sized blooms with white ray florets and prolific branching; natural season flowering date September 9-13 (week 37); blooming for a period of 5 weeks.

3 Drawing Sheets

Botanical designation: *Chrysanthemum×morifolium* Ramat.

Cultivar denomination: 'Zanmuceles'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmuceles'. 'Zanmuceles' is a product of a breeding and selection program for outdoor pot mums (garden mums) which had the objective of creating new cultivars with a double type inflorescence, a natural season flowering date around week 37, blooming for a period of 5 weeks. 'Zanmuceles' is a seedling resulting from a cross of the female parent id 30549 (not patented) with the male parent id 26356 (not patented). Plants of the new cultivar 'Zanmuceles' differ from plants of its parent plants in growth habit. The female parent has a more compact shape than the seedling, while the male parent is more spreading than the seedling.

The new and distinct cultivar was discovered and selected as a flowering plant by Henricus Cornelius Maria Jacobs on a cultivated field in Rijsenhout, The Netherlands in 2010. The first act of asexual production of 'Zanmuceles' was accomplished when vegetative cuttings from the initial selection in 2010 were propagated further in a controlled environment in Rijsenhout, The Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *chrysanthemum* (of about 12 weeks) is shown in the accompanying drawings, the color being as nearly true as possible with color photographs of this type.

DESCRIPTION OF THE INVENTION

Figure 1:
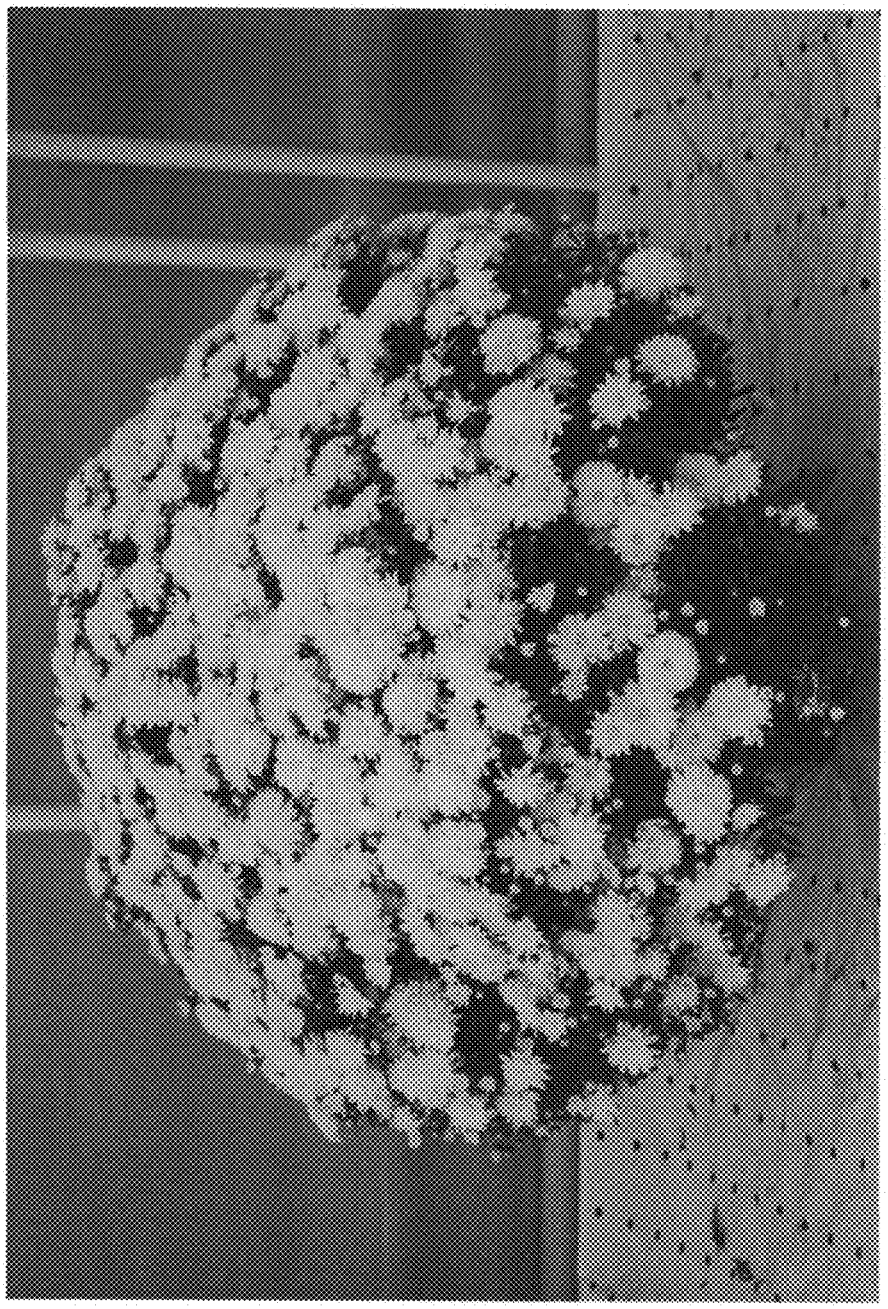
FIG. 1 shows a plant of the cultivar in full bloom.
Figure 2:
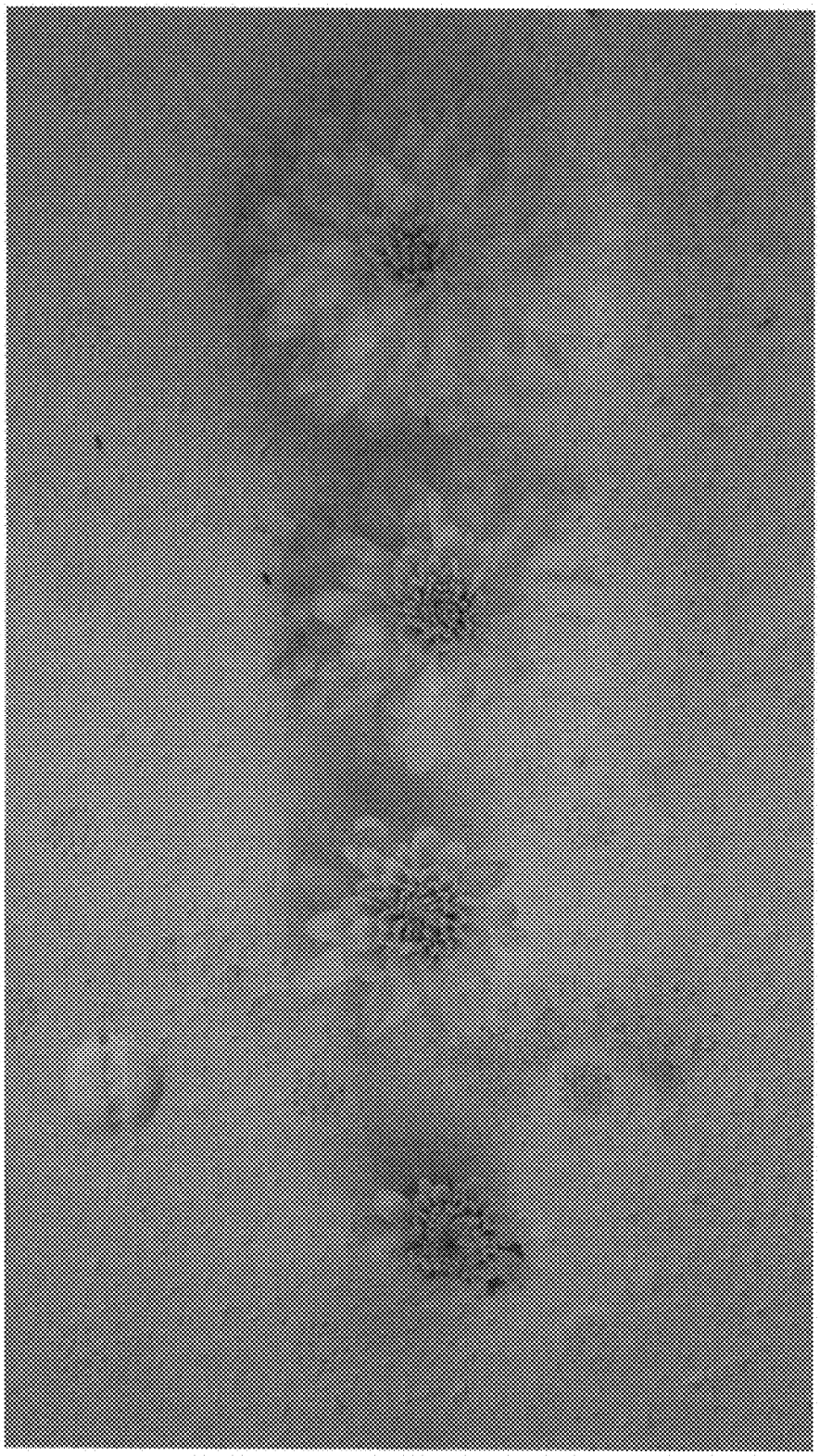
FIG. 2 shows the various stages of bloom of the new cultivar.
Figure 3:
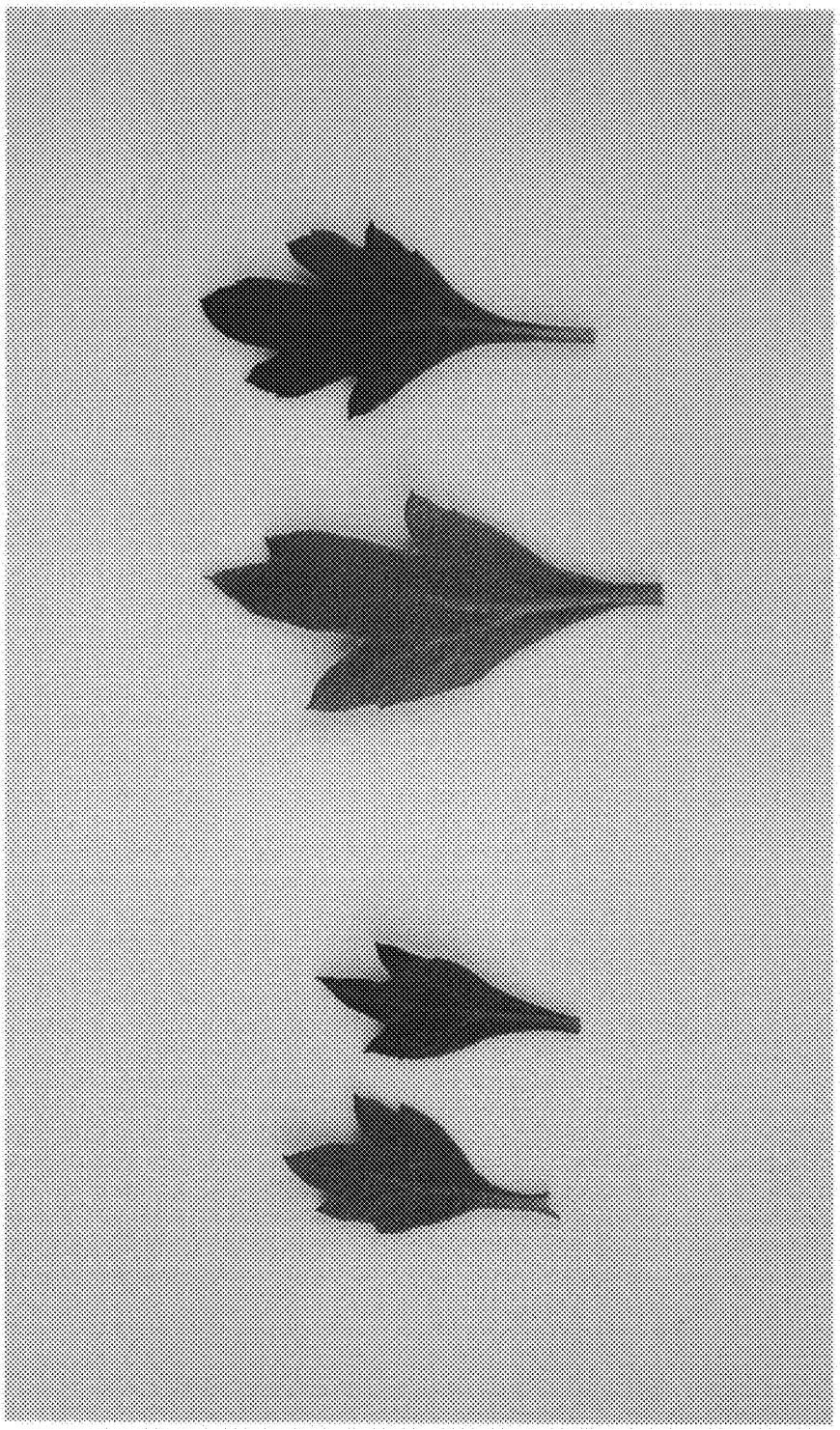
FIG. 3 shows the various stages of foliage of the new cultivar.

The observations and measurements were gathered from plants, in the period of 11 to 18 weeks of age, grown outdoor in Rijsenhout, The Netherlands under natural day length and temperature and planted in week 23 in 2013 (with a warm summer), receiving drip irrigation. The natural blooming date of this crop was September 9-13 (week 37). The average height of the plants was 40-45 cm. No growth retardants were used. No tests were done on disease or insect resistance or susceptibility. No tests were done on cold or drought tolerance. This new variety produces medium sized blooms with white ray florets blooming for a period of 5 weeks.

From the cultivars known to the inventor the most similar existing cultivar in comparison to 'Zanmuceles' is 'Crete' (U.S. Plant Pat. No. 16,677). When 'Crete' and 'Zanmuceles' are being compared the following difference is noticed: The difference of 'Crete' and 'Zanmuceles' are (1) Inflorescence size. And (2) Inflorescence color. (1). Inflorescences of 'Crete' are smaller than those of 'Zanmuceles'. (2) The inflorescences of 'Crete' are cream colored, while those of 'Zanmuceles' are pure white.

The following is a description of the plant and characteristics that distinguish 'Zanmuceles' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, 5th edition 2007.

TABLE 1

Botanical Description of *Chrysanthemum* × *morifolium* Ramat. 'Zanmuceles'

| | |
|---|---|
| **Bud** | |
| Size: | Small; cross-section 5-6 mm, height 4 mm |
| Shape: | Round |
| Texture: | Pubescent |
| Outside color: | Greyed-green 191A |
| **Phyllaries** | |
| Number: | 21, arranged in 3 rows |
| Shape: | Elliptic |
| Apex: | Acute |
| Base: | Truncate |
| Margin: | Entire |
| Color: | Upper side: Green N138A<br>Lower side: Green 138A |
| Length and width: | 5-6 mm; 1.5-2 mm |
| Texture: | Pubescent |
| **Inflorescences** | |
| Type: | Double |
| Height: | 1.8 cm |
| Diameter: | 5 cm |
| Peduncle length: | 10-12 cm |
| Peduncle color: | Green 138B |
| Peduncle diameter: | 1.5.mm |
| Peduncle texture: | Pubescent |
| Peduncle strength: | Weak |
| Number per branch: | About 5-6 .inflorescences |
| Duration of flowering: | 5 weeks |
| Seeds: | Produced in small quantities, ovate, Greyed-brown 199A, length 1.5 mm, diameter 0.5 mm; texture: rough with ribs |
| Fragrance: | Faint chrysanthemum odor |
| **Color inflorescences** | |
| Center of inflorescence: | Immature stage: White 155A; Mature stage: White 155A |
| Color of upper side of ray florets: | White NN155D |
| Color of lower side of ray florets: | White NN155D |
| Tonality from distance: | A garden mum with white blooms and a cream center |
| Color of ray florets after aging of the plant: | White 155D |
| **Ray florets** | |
| Type: | Ligulate |
| Texture: | Upper and lower side smooth |
| Number: | 190-210 |
| Shape: | elliptic |
| Apex: | dentate |
| Base: | attenuate |
| Cross-section: | flat |
| Longitudinal axis: | reflexing |
| Length of corolla tube: | 3-5 mm |
| Diameter corolla tube: | 1-1.5 mm |
| Ray floret margin: | Entire |
| Ray floret length: | 1.5-2.5 cm |
| Ray floret width: | 1-5 mm |
| Ratio length/width: | High |
| Disc florets | Absent |
| **Receptacle** | |
| Color: | Yellow-green 145D |
| Shape: | Conical raised |
| Height: | 4 mm |
| Diameter: | 3 mm |
| **Reproductive Organs** | |
| Androecium: | Absent |
| Pollen: | Absent |
| Gynoecium: | Present on ray florets |

TABLE 1-continued

Botanical Description of *Chrysanthemum* × *morifolium* Ramat. 'Zanmuceles'

| | |
|---|---|
| Style color: | Yellow-green 154C |
| Style length: | 4 mm |
| Stigma color: | Yellow 7A |
| Stigma width: | 1 mm |
| Ovary: | Enclosed in calyx; color: Yellow-green 149D |
| **Plant** | |
| Type: | Bushy |
| Growth habit: | Spherical shape |
| Growth rate: | Medium to High |
| Height: | 40-45 cm |
| Width: | 55-65 cm |
| Stem color: | Greyed-brown 199A |
| Stem strength: | Weak |
| Stem brittleness: | Brittle |
| Stem anthocyanin coloration: | Absent |
| Internode length: | 1-2.5 cm |
| Length of lateral branch: | From top to bottom 22-25 cm |
| Lateral branch color: | Green 137 C |
| Lateral branch, attachment: | weak |
| Lateral branch diameter: | 2.5 mm |
| Lateral branch texture: | Pubescent with ribs |
| Branching (average number of lateral branches): | Dense with 8 breaks after pinching |
| Natural season blooming date: | Sep. 9-13 (week 37) in Rijsenhout, The Netherlands |
| Roots-habits: | Fine, freeling branching |
| Roots-color: | White 155D |
| **Foliage** | |
| Glossiness: | Leaf upper side: weak<br>Leaf lower side: very weak |
| Leaf color: | Upper side: Green 138A<br>Lower side: Green 138B |
| Color midvein: | Upper side: Yellow-green 147D<br>Lower side: Yellow-green 148D |
| Size: | Small; length 2-3.5cm, width 1-1.3 cm |
| Quantity (number per lateral branches): | 24-26 |
| Shape: | Elliptic |
| Texture upper side: | Sparsely pubescent |
| Texture under side: | Pubescent |
| Venation arrangement: | Palmate |
| Shape of margin: | Serrated |
| Shape of base of sinus between lateral lobes: | Rounded |
| Margin of sinus between lateral lobes: | Diverging |
| Shape of base: | Acute |
| Apex: | Mucronulate |
| Petiole attitude: | Moderately upwards |
| Petiole length: | 0.3-0.5 cm |
| Petiole diameter: | 2-3 mm |
| Petiole color: | Yellow-green 147D |
| Stipule: | Small, 1 mm |

TABLE 2

Differences with the comparison variety, when grown under identical conditions

| | 'Zanmuceles' | 'Crete' |
|---|---|---|
| Inflorescence size | 5 cm | 3 cm |
| Color upper side ray florets | White NN155D | White 158D |

I claim:

1. A new and distinct *chrysanthemum* plant named 'Zanmuceles' as described and illustrated.

* * * * *